(12) United States Patent
Turner

(10) Patent No.: US 10,548,811 B2
(45) Date of Patent: Feb. 4, 2020

(54) VALVE FOR FLUID FLOW ASSEMBLY

(71) Applicant: R. Scott Turner, Palmerton, PA (US)

(72) Inventor: R. Scott Turner, Palmerton, PA (US)

( * ) Notice: Subject to any disclaimer, the term of this patent is extended or adjusted under 35 U.S.C. 154(b) by 0 days.

(21) Appl. No.: 15/864,247

(22) Filed: Jan. 8, 2018

(65) Prior Publication Data

US 2018/0193226 A1    Jul. 12, 2018

Related U.S. Application Data

(60) Provisional application No. 62/467,991, filed on Mar. 7, 2017, provisional application No. 62/444,025, filed on Jan. 9, 2017.

(51) Int. Cl.
| | | |
|---|---|---|
| *A61J 1/14* | (2006.01) | |
| *A61M 39/26* | (2006.01) | |
| *A61J 1/10* | (2006.01) | |
| *A61J 15/00* | (2006.01) | |

(52) U.S. Cl.
CPC ............... *A61J 1/1475* (2013.01); *A61J 1/10* (2013.01); *A61M 39/26* (2013.01); *A61J 15/0015* (2013.01)

(58) Field of Classification Search
CPC ............ A61M 39/26; A61M 2039/266; A61M 2039/267; A61M 2039/268; A61M 2039/085; A61M 2039/246; A23L 33/40
See application file for complete search history.

(56) References Cited

U.S. PATENT DOCUMENTS

| | | |
|---|---|---|
| 4,560,387 A | 12/1985 | Defago et al. |
| 4,722,850 A | 2/1988 | White et al. |
| 5,018,646 A | 5/1991 | Billman et al. |
| 5,137,257 A | 8/1992 | Tice |
| 5,372,578 A | 12/1994 | Kriesel et al. |
| 5,509,433 A * | 4/1996 | Paradis ...................... A61J 1/18 137/1 |
| 6,319,243 B1 * | 11/2001 | Becker .................. A61J 1/2093 206/221 |

(Continued)

FOREIGN PATENT DOCUMENTS

| | | |
|---|---|---|
| CA | 2974758 | 8/2016 |
| DE | 10 2010 026 848 | 1/2012 |

(Continued)

OTHER PUBLICATIONS

Medicina Online Catalog, FlexiFeed Enternal Feeding bags and Gravity Sets, Item No. FB250, Jul. 28, 2013, http://www.medicina.co.uk/accessories/flexi.htm (1 page).

(Continued)

*Primary Examiner* — Nathan R Price
*Assistant Examiner* — Melissa A Snyder
(74) *Attorney, Agent, or Firm* — Massina Pat. & TM Law

(57) ABSTRACT

A feeding pouch assembly includes a pouch defining a fluid chamber with an outlet port extending from the pouch. The outlet port is in fluid communication with the fluid chamber. A valve is positioned at the outlet port and is biased to a natural sealing position wherein flow from the fluid chamber to the outlet port is prevented. The valve moves to a non-sealing position, wherein fluid is free to flow from the fluid chamber to the outlet, upon connection of the outlet port to a feeding tube. The valve automatically moves to the sealing position upon disconnection of the feeding tube from the outlet port.

12 Claims, 5 Drawing Sheets

(56) References Cited

U.S. PATENT DOCUMENTS

| | | |
|---|---|---|
| 6,488,171 B1 | 12/2002 | Diveley |
| 8,136,330 B2 | 3/2012 | Ostler et al. |
| 8,231,597 B2 | 7/2012 | Knight |
| 2004/0011760 A1 | 1/2004 | Schupp et al. |
| 2005/0269358 A1 | 12/2005 | Choi |
| 2007/0062904 A1 | 3/2007 | Beaudette |
| 2008/0319391 A1 | 12/2008 | Jackson |
| 2011/0118676 A1 | 5/2011 | Kropczynski, Jr. et al. |
| 2012/0074146 A1* | 3/2012 | Kunishige .......... A61M 39/1011 220/315 |
| 2012/0094901 A1 | 4/2012 | Ludwig et al. |
| 2012/0150140 A1 | 6/2012 | Ginzburg et al. |
| 2012/0310177 A1 | 12/2012 | Becker |
| 2014/0114259 A1 | 4/2014 | Durham |
| 2015/0225131 A1 | 8/2015 | Gewirtz |
| 2017/0105903 A1* | 4/2017 | Gallotto ................ A61L 29/048 |

FOREIGN PATENT DOCUMENTS

| | | |
|---|---|---|
| WO | WO 2012/137286 | 11/2012 |
| WO | WO 2012/150632 | 11/2012 |

OTHER PUBLICATIONS

Cleveland Clinic, Tube-Feeding Instructins for Home, Jul. 12, 2012, Cleveland Clinic http://my.clevelandclinic.org/ccf/media/files/Digestive_Disease/center-human-nutrition/home-enternal-nutrition-booklet.pdf.

\* cited by examiner

VALVE FOR FLUID FLOW ASSEMBLY

This application claims the benefit of U.S. Provisional Application No. 62/444,025, filed on Jan. 9, 2017, and U.S. Provisional Application No. 62/467,99, filed on Mar. 15, 2017, the contents of each of which are incorporated herein in their entirety.

FIELD OF THE INVENTION

The present invention relates to a valve. More particularly, the present invention relates to a valve positionable within a tube and with a projecting portion moveable relative to the tube between a sealing position and an open position. The present invention will be described with respect to a percutaneous endoscopic gastrostomy (PEG) feeding assembly, however, the valve of the present invention is not limited to such and may be utilized in various fluid assemblies.

BACKGROUND OF THE INVENTION

PEG is an endoscopic medical procedure in which a tube (PEG tube) is placed into a patient's stomach through the abdominal wall, most commonly to provide a means of feeding when oral intake is not adequate. This provides enteral nutrition (making use of the natural digestion process of the gastrointestinal tract) despite bypassing the mouth. In addition to the PEG procedure, a gastrostomy feeding tube may be placed using an open surgical gastrostomy insertion procedure.

Referring to FIG. 1, the PEG tube 10 typically extends from a site 12 on the patient's abdomen 14. The opposite end of the tube 10 includes a connection fitting 16 or the like with one or more ports 17 for connection of a supply or extraction apparatus. A clamp 18 may be positioned along the tube 10 to seal the tube 10. Once the PEG tube is installed, the patient may be fed, provided medicine or the like through one of the ports 17. In the illustrated embodiment, the port 17 includes an extending tube 20.

As described in U.S. patent application Ser. No. 14/444,387, which is incorporated herein by reference, a pouch 30 filled with feeding fluid 32 may be connected with a port 17 of the PEG feeding tube 10 via a connector 34 configured to engage the connection fitting 16. While the pouch 30 improves the feeding procedure, it is desirable to provide a reliable, easy to use valve within the connector 34 to prevent spillage of the fluid 32 prior to connection with, and after disconnection from, the port 17.

SUMMARY OF THE INVENTION

In at least one embodiment, the present invention provides a feeding pouch assembly includes a pouch defining a fluid chamber with an outlet port extending from the pouch. The outlet port is in fluid communication with the fluid chamber. A valve is positioned at the outlet port and is biased to a natural sealing position wherein flow from the fluid chamber to the outlet port is prevented. The valve moves to a non-sealing position, wherein fluid is free to flow from the fluid chamber to the outlet, upon connection of the outlet port to a feeding tube. The valve automatically moves to the sealing position upon disconnection of the feeding tube from the outlet port.

In at least one embodiment, the present invention provides a feeding assembly including a feeding pouch and a feeding tube. The feeding pouch defines a fluid cavity and an outlet port. The outlet port includes a first tubular portion and a second tubular portion with the second tubular portion having an internal diameter smaller than an internal diameter of the first tubular portion with a shoulder defined between the first and second tubular portions. The feeding tube includes an inlet having a tubular member configured to be received within the second tubular portion. A valve is positioned within the outlet port. The valve includes a substantially hollow valve body extending from a generally open end to a substantially closed end. The closed end includes a central portion supported relative to the valve body by a resiliently flexible angled portion such that the central portion is biased to an extended position but is moveable to a position within the valve body. One or more holes extend through the angled portion, otherwise the closed end is sealed. In the extended position, the central portion and/or the angled portion seals against the shoulder and in the position within the valve body, a fluid passage is defined from the fluid chamber, through the one or more holes, to the second tubular portion and to the feeding tube tubular member.

In at least one embodiment, the invention provides a method of providing a feeding to a patient that has a feeding tube extending therefrom, the feeding tube having an inlet, the method including connecting an outlet port extending from a feeding pouch to the feeding tube inlet, the outlet port in fluid communication with a fluid chamber within the feeding pouch; extending a portion of the feeding tube inlet into the outlet port such that a valve positioned at the outlet port and biased to a natural sealing position, wherein flow from the fluid chamber to the outlet port is prevented, is moved to a non-sealing position, wherein fluid is free to flow from the fluid chamber to the outlet; and delivering fluid from fluid chamber through the valve and into the feeding tube.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
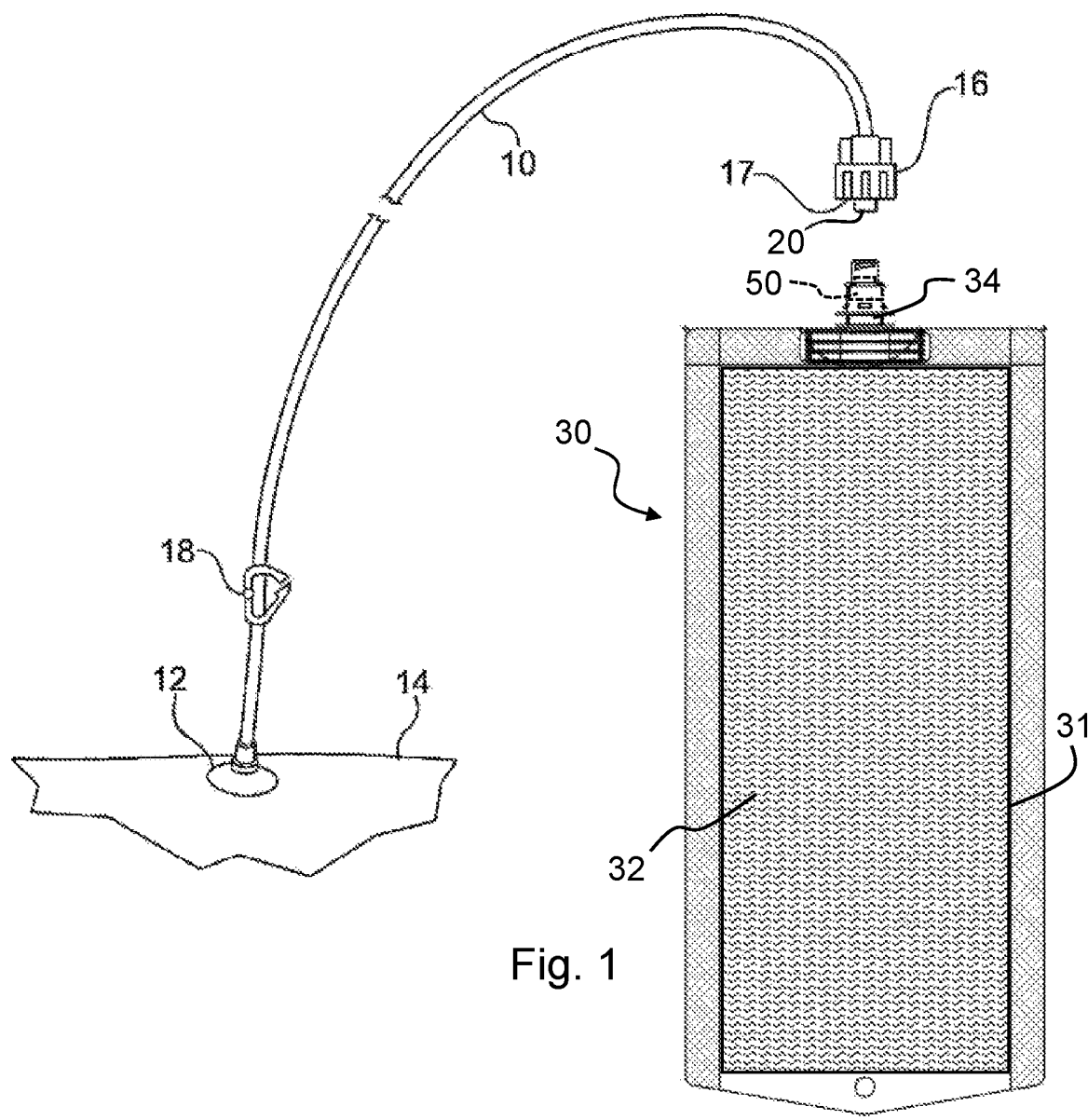
FIG. 1 is a perspective view illustrating an exemplary filled pouch prior to connection to a PEG feeding tube, the pouch incorporating a valve in accordance with an embodiment of the invention.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Figures 7, 8:
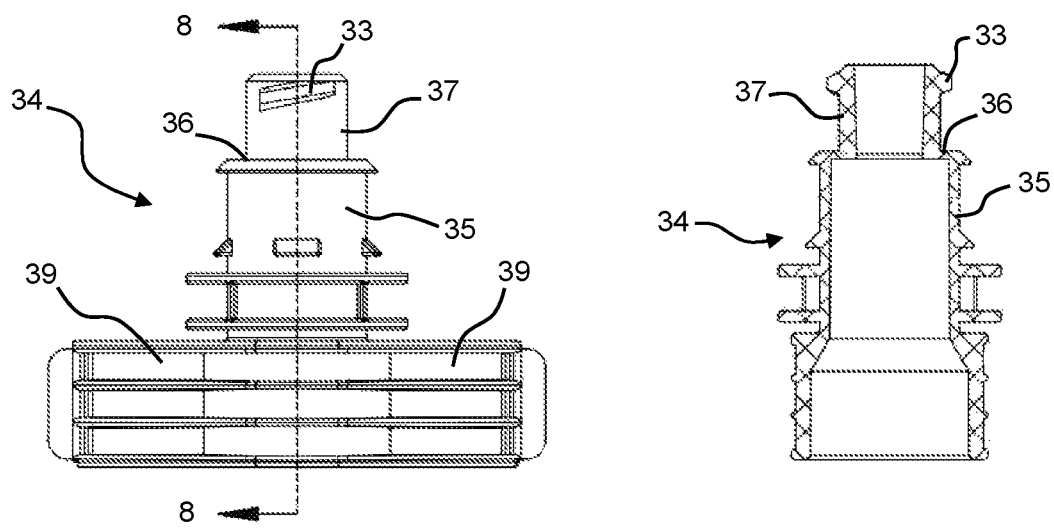
FIG. 7 is an elevation view of an exemplary connector.
FIG. 8 is a cross-sectional view along the line 8-8 in FIG. 7.

Referring to FIGS. 1 and 7-8, an illustrative pouch 30 and connector 34 will be described. The pouch 30 defines an internal chamber 31 configured to be filled with a fluid 32. In the illustrated embodiment, the pouch 30 is formed about the connector 34 such that the connector 34 is integrated therewith. In the illustrated embodiment, the connector 34 includes outwardly extending flanges 39 which extend along and are sealed within an edge of the pouch 30. Other methods of connecting the connector 34 with the pouch 30 may also be utilized. The connector 34 includes a first tubular portion 35 which joins with a second tubular portion 37 at a shoulder 36. The second tubular portion 37 has a smaller diameter than the first tubular portion 35. As will be described in more detail hereinafter, the valve 50 is positioned within the first tubular portion 35 such that the valve 50 controllably seals against fluid passage from the first tubular portion 35 to the second tubular portion 37. In the illustrated embodiment, the second tubular portion 37 includes external threads 33 configured for engagement with the port 17. A foil seal or the like (not shown) may be positioned over the open end of the second tubular portion 37 as a tamper evident seal. Due to the valve 50, the foil seal is not necessary to prevent leakage from the chamber 31.

The chamber 31 of the pouch 30 may have any desired volume. In at least one embodiment, the chamber 31 has a volume that is equal to or greater than a single serving, for example, equal to or greater than 250 ml. With a reliable self-sealing valve 50, if the fluid 32 is not completely dispensed in a single feeding, the pouch 30 is automatically sealed upon disconnection from the port 17 and the remaining contents may be stored for future use. The pouch 30 is preferably configured with an elongate configuration, for example, having a length at least twice the width of the pouch 30, which aids in expelling of the fluid. The length to width ratio of the pouch 30 is preferably in a range of about 2.0:1 to 3.5:1, and may more preferably be about 2.7:1.

Figure 2:
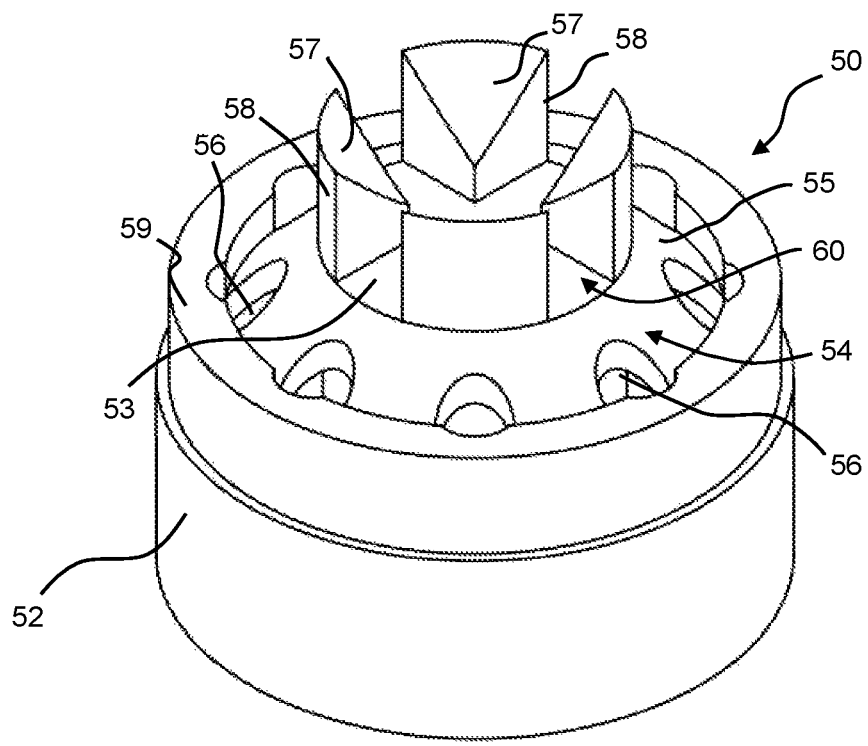
FIG. 2 is a perspective view of an exemplary embodiment of a valve in accordance with an embodiment of the invention.
Figure 3:
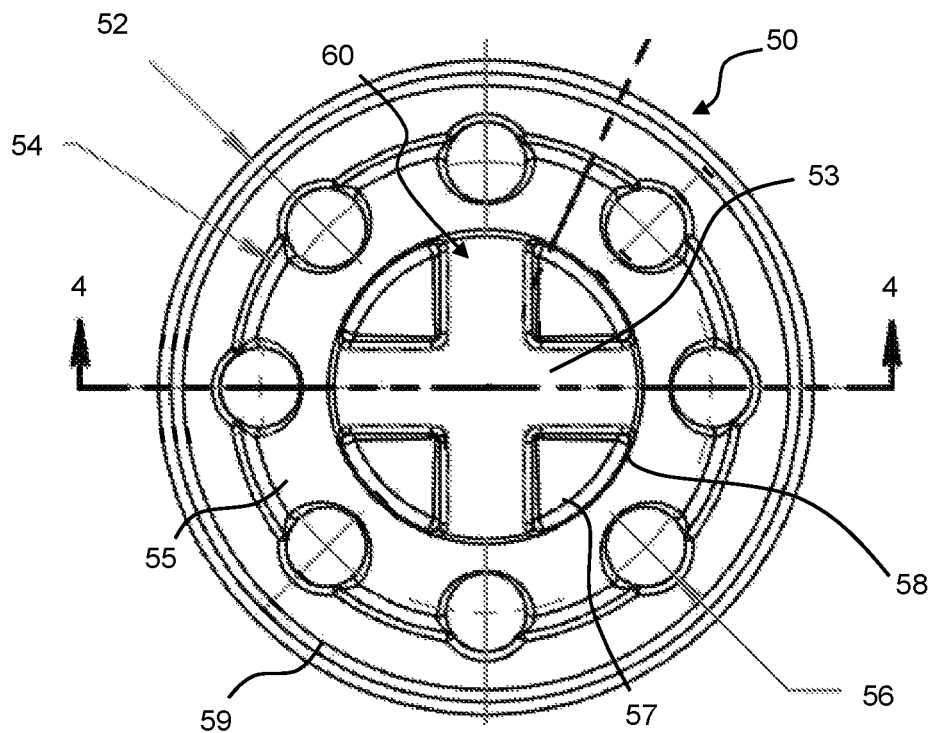
FIG. 3 is a top plan view of the valve of FIG. 2.
Figure 4:
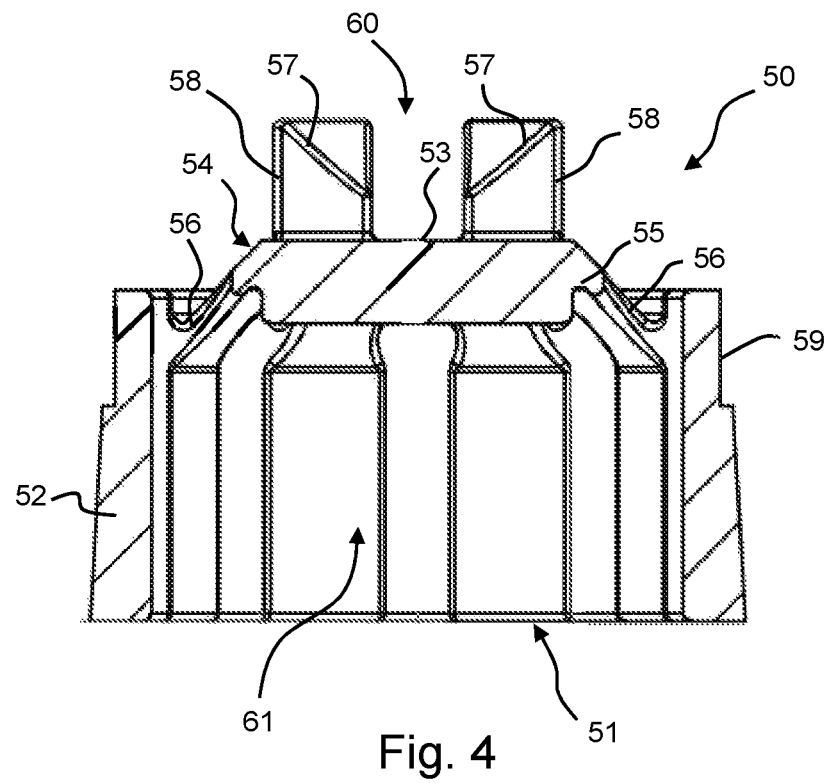
FIG. 4 is a cross-sectional view along the line 4-4 in FIG. 3.

Referring to FIGS. 2-4, an exemplary valve 50 in accordance with an embodiment of the invention will be described. The valve 50 includes a hollow body 52 extending from a generally open end 51 to a substantially closed end 54 with an internal chamber 61 defined between the ends 51, 54. The substantially closed end 54 includes a planar central portion 53 supported by an angled outer portion 55. A series of holes 56 extend through the angled outer portion 55, and may extend into the wall of the hollow body 52 as illustrated, otherwise the closed end 54 is sealed.

The angled portion 55 is resiliently flexible and biases the central portion 53 toward an extended natural position as shown in FIG. 4. By natural position, it is meant to be the position of the central portion 53 relative to the hollow body 52 when no bias overcoming force is applied to the central portion 53. The resiliently flexible nature of the angled portion 55 is such that the central portion 53 may be moved toward and within the hollow body 52 (see FIG. 6) when a bias overcoming force is applied thereto and then return to the natural extended position (see FIG. 4) when the force is removed. The dimensions of the angled portion 55 and the hollow body 52 may be controlled to defined the desired amount of resiliency. In the illustrated embodiment, the hollow body 52 includes thinned areas 59 near the angled portion 55 to facilitate a desired resiliency.

Again referring to FIGS. 2-4, a series of spaced apart projections 58 extend from the central portion 53 with spaces 60 therebetween. The spaces 60 allow fluid to flow past the projections 58. In the illustrated embodiment, each projection 58 includes a tapered face 57 such that the tapered faces 57 of the various projections 58 define a central tube guiding area. The tapered faces are not required and the projections 58 may present a flat surface. As another alternative, it is also contemplated that the projections are not necessary and the tube 20 may directly contact the central portion 53 provided the end of the tube 20 has side holes or the like (not shown) to allow fluid to flow to the inside passage 24 of the tube 20.

Figure 5:
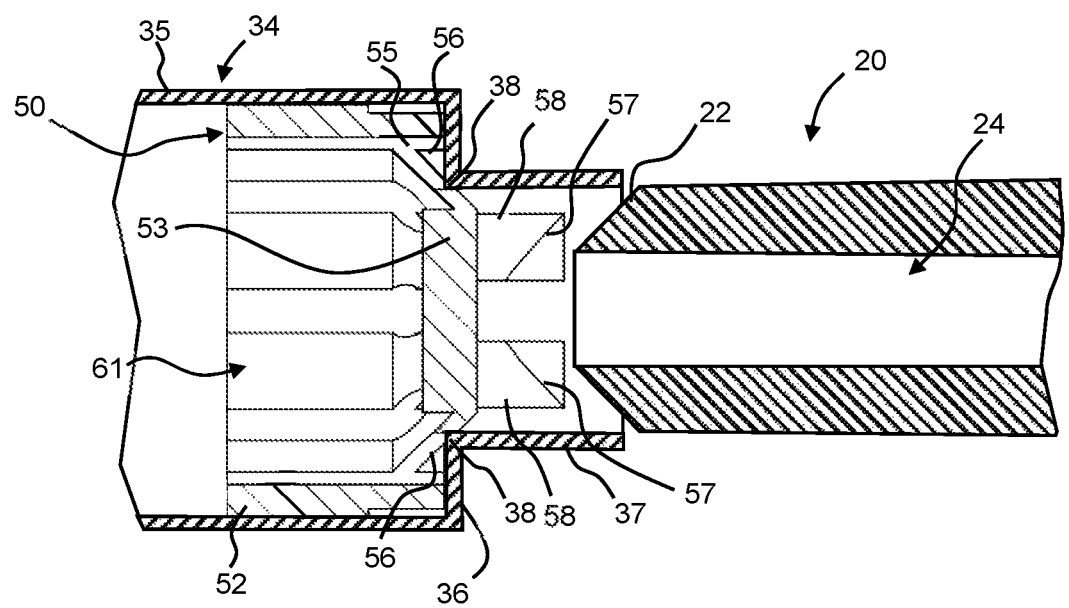
FIG. 5 is a cross-sectional view illustrating the valve positioned within the connector of the pouch in a closed, sealing position.

Referring to FIG. 5, the valve 50 is shown positioned within an exemplary connector 34 of the pouch 30 as described above. The valve body 52 complements the size and configuration of the inside of the first tubular portion 35 such that the valve body 52 generally seals against the inside surface of the first tubular portion 35. As illustrated in FIG. 4, the valve body 52 may taper outwardly, for example at a taper of about 3°, to further enhance the seal against the inside surface of the first tubular portion 35. The fluid pressure within the pouch 30 exerts a force within the internal chamber 61 of the valve body 52 which causes the valve body 52 to further self-seat against the inside of the first tubular portion 35 and the shoulder 36.

The valve 50 is positioned such that the planar central portion 53 and projections 58 extend into the second tubular portion 37 of the connector 34 while the angled portion 55 engages the shoulder 36 as at 38 and thereby seal the first tubular portion 35 and thereby the connector 34. As set forth above, the angled portion 55 has a resiliency thereto and as a result, is biased into engagement with the shoulder 36 and may even compress slightly against the shoulder 36 at the seal area 38. Accordingly, while the holes 56 may allow fluid to flow from within the hollow body 52, the fluid is prevented from flowing into the second tubular portion 37 due to the sealing engagement of the central portion 53 with the shoulders 36. The central portion 53 is maintained in this closed, sealing position until a bias overcoming force is applied to the central portion 53.

Figure 6:
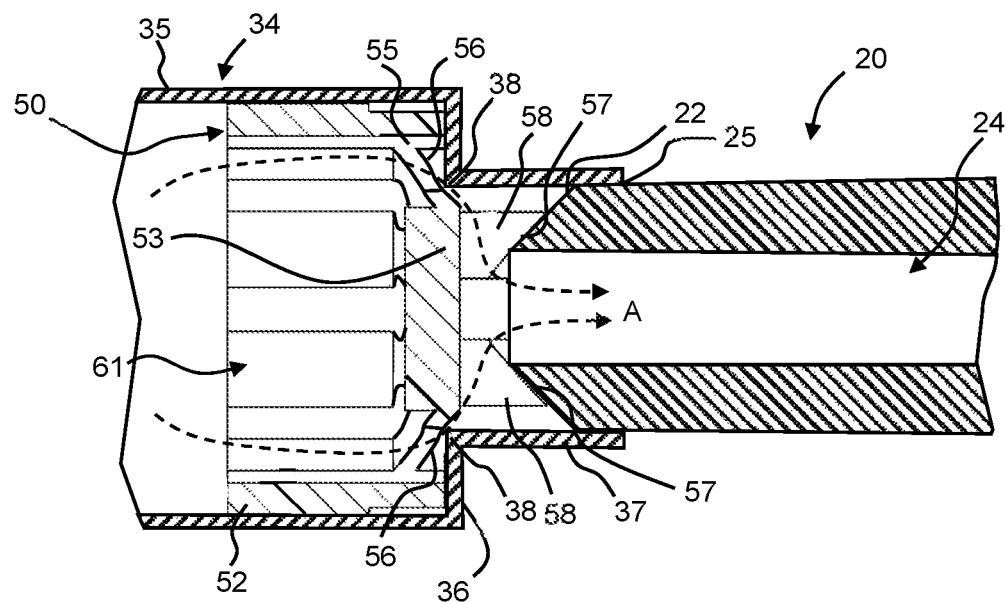
FIG. 6 is a cross-sectional view illustrating a tube portion of the PEG feeding tube port engaging the valve and moving the valve to an open position.

FIG. 6 illustrates the tubular portion 20 of the port 17 (see FIG. 1) extending into the second tubular portion 37 of the connector 34. As the tubular portion 20 is inserted, it contacts the projections 58 and forces the planar central portion 53 into the hollow body 52. In the illustrated embodiment, the tubular portion 20 has a tapered tip 22 which complements the tapered faces 57 of the projections 58. As the central portion 53 moves inward to the interior of the hollow body 52, the central portion 53 and angled portion 55 disengage from the seal area 38 at the shoulder 36. As such, fluid is free to flow into the internal chamber 61, through the holes 56 and through the spaces 60 into the passage 24 of the tubular portion 20, as indicated by the arrows A in FIG. 6.

It is noted that the outside surface of the tubular portion 20 seals against the second tubular portion 37 at seal area 25 as illustrated in FIG. 5. The outside surface of the tubular portion 20 preferably has a slight taper, for example, 1°, such that the tubular portion 20 has to enter the second tubular portion 37 before there is contact at the seal area 25. The flexible nature of the angled portion 55 facilitates a relatively large range of motion of the central portion 53 which allows the tubular portion 20 to be inserted a necessary amount to seal at the seal area 25, including compensating for manufacturing tolerances.

Once the tubular portion 20 is removed, the resilient nature of the angled portion 55 will bias the central portion 53 back to the natural position illustrated in FIG. 4 and the passage through the connector 34 will once again be sealed.

Figure 9:
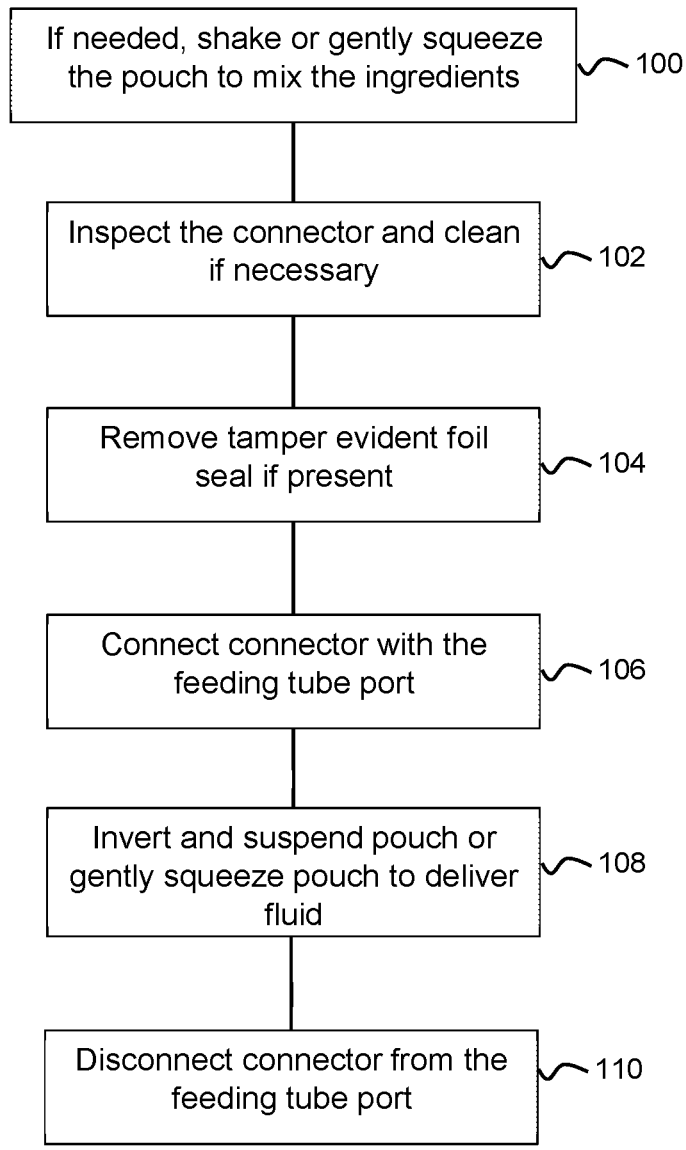
FIG. 9 is a flow chart illustrating an exemplary method of feeding in accordance with an embodiment of the invention.

Having generally described the components of the pouch assembly, an illustrative method of providing a feeding to a patient having a feeding tube with a pouch assembly in accordance with an embodiment of the disclosure will be described with reference to FIG. 9. If needed, at step 100, the user may shake or gently squeeze the pouch 30 to mix the ingredients. At step 102, the user visually inspects the connector 34 to ensure no dirt or debris is present and cleans the connector 34, if necessary. If a tamper evident foil seal is present, the foil seal is removed at step 104. At step 106, the connector 34 is connected with the feeding tube port 17. Upon connection, a portion 20 of the feeding tube inlet port 17 extends into the outlet port of the connector 34 and contacts the valve 50 such that the valve 50 is moved to a non-sealing position, wherein fluid is free to flow from the fluid chamber of the pouch 30 to the port 17. At step 108, the pouch 30 may be inverted and suspended to gravity feed, or may be gently squeezed if conducting a bolus feeding. Upon completion of the feeding, the connector 34 is disconnected from the port 17 at step 110. Upon disconnection, the valve 50 automatically moves to the sealing position and any fluid remaining in the fluid chamber is sealed within the fluid chamber. If the contents are not completely utilized, they may be refrigerated or otherwise stored until utilized for a second feeding. Such a second feeding begins at step 106.

While the valve 50 is described herein in conjunction with a PEG pouch assembly, the invention is not limited to such. The valve 50 may be utilized in any junction wherein one of the tubes includes a shoulder upon which the central portion 53 may seat and the other of the tubes extends into the first of the tubes and engages the central portion 53 to move it to an open position.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A feeding pouch assembly comprising:
  a pouch defining a fluid chamber;
  an outlet port extending from the pouch, the outlet port in fluid communication with the fluid chamber, the outlet port defining an internal shoulder; and
  a valve positioned at the outlet port, the valve comprising a substantially hollow valve body defined by a continuous circumferential member extending from a generally open end to a substantially closed end, the continuous circumferential member having a height from the open end to the substantially closed end, the closed end including a central portion supported relative to the valve body by a resiliently flexible angled portion such that the central portion is biased to an extended position but is moveable to a retracted position within the valve body, a distance between the extended position and the retracted position being smaller than the height of the continuous circumferential member, and one or more holes extend through the angled portion, otherwise the closed end is sealed, wherein
  the valve is biased to a natural sealing position, wherein the central portion and/or angled portion seal against the internal shoulder and flow from the fluid chamber to the outlet port is prevented, the valve moving to a non-sealing position, wherein fluid is free to flow from the fluid chamber to the outlet, upon connection of the outlet port to a feeding tube, and the valve automatically moving to the sealing position upon disconnection of the feeding tube from the outlet port.

2. The feeding pouch assembly according to claim 1 wherein a fluid path extends through the one or more holes extending through the angled portion when the valve is in the non-sealing position.

3. The feeding pouch assembly according to claim 1 wherein the valve includes one or more projections extending outwardly from the central portion.

4. The feeding pouch assembly according to claim 1 wherein the outlet port has an external thread configured for threaded engagement with an inlet of the feeding tube.

5. The feeding pouch assembly according to claim 1 wherein the fluid chamber is sized to hold a volume larger than a single feeding.

6. A feeding assembly comprising:
  a feeding pouch defining a fluid cavity and an outlet port, the outlet port including a first tubular portion and a second tubular portion, the second tubular portion having an internal diameter smaller than an internal diameter of the first tubular portion with a shoulder defined between the first and second tubular portions;
  a feeding tube including an inlet having a tubular member configured to be received within the second tubular portion; and
  a valve positioned within the outlet port, the valve comprising a substantially hollow valve body defined by a continuous circumferential member extending from a generally open end to a substantially closed end, the closed end including a central portion supported relative to the valve body by a resiliently flexible angled portion which extends radially inward from the continuous circumferential member such that the central portion is biased to an extended position but is moveable to a position within the valve body, wherein one or more holes extend through the angled portion, otherwise the closed end is sealed,
  wherein in the extended position, the central portion and/or the angled portion seals against the shoulder and in the position within the valve body, a fluid passage is defined from the fluid chamber, through the one or more holes, to the second tubular portion and to the feeding tube tubular member.

7. The feeding assembly according to claim 6 wherein upon connection of the outlet port with the inlet, the feeding tube tubular member causes the central portion to move to the position within the valve body.

8. The feeding assembly according to claim 7 wherein upon disconnection of the outlet port with the inlet, the central portion automatically moves to the extended position.

9. The feeding assembly according to claim 6 wherein the valve includes one or more projections extending outwardly from the central portion and upon connection of the outlet port with the inlet, the feeding tube tubular member contacts the one or more projections which causes the central portion to move to the position within the valve body.

10. The feeding assembly according to claim 7 wherein upon connection of the outlet port with the inlet, the feeding tube tubular member contacts the central portion to cause the central portion to move to the position within the valve body.

11. The feeding assembly according to claim 6 wherein the outlet port and the inlet have a threaded interconnection.

12. The feeding assembly according to claim 6 wherein the fluid chamber is sized to hold a volume larger than a single feeding.

* * * * *